United States Patent
Yamamoto

(10) Patent No.: US 7,887,652 B2
(45) Date of Patent: Feb. 15, 2011

(54) MANUFACTURING METHOD OF ABSORBENT ARTICLE

(75) Inventor: Hiroki Yamamoto, Kanonji (JP)

(73) Assignee: Uni-Charm Corporation, Ehime (JP)

( * ) Notice: Subject to any disclaimer, the term of this patent is extended or adjusted under 35 U.S.C. 154(b) by 175 days.

(21) Appl. No.: 12/389,947

(22) Filed: Feb. 20, 2009

(65) Prior Publication Data

US 2010/0096065 A1    Apr. 22, 2010

(30) Foreign Application Priority Data

Oct. 21, 2008    (JP) ................. 2008-271124

(51) Int. Cl.
*B32B 37/00*    (2006.01)
(52) U.S. Cl. ...................... 156/64; 156/73.1
(58) Field of Classification Search .............. 156/64, 156/73.1, 250, 267, 269, 580.1, 580.2; 228/1.1, 228/110.1; 264/442, 443, 444, 445
See application file for complete search history.

(56) References Cited

U.S. PATENT DOCUMENTS 7,004,373 B1 * 2/2006 Miller .................. 228/103
7,225,965 B2 * 6/2007 Johansen ................. 228/1.1
7,234,355 B2 * 6/2007 Dewangan et al. .......... 73/622

FOREIGN PATENT DOCUMENTS

JP         06-341966 A    12/1994

* cited by examiner

*Primary Examiner*—James Sells
(74) *Attorney, Agent, or Firm*—Lowe, Hauptman, Ham & Berner, LLP

(57) ABSTRACT

The manufacturing method of an absorbent article according to the present invention includes: a step A of bonding, by using an ultrasonic bonding device, a continuum of a front waistband region and a continuum of a rear waistband region in predetermined regions each corresponding to a bonded region of the front waistband region and the rear waistband region after overlapping the continuum of the front waistband region and the continuum of the rear waistband region under conveyance; a step B of outputting a first predetermined signal indicating a failure state when it is determined that an output signal from the ultrasonic bonding device does not satisfy a first specified condition; and a step C of outputting a second predetermined signal indicating a failure state when it is determined that a bonded area in any of the predetermined regions does not satisfy a second specified condition.

7 Claims, 10 Drawing Sheets

MANUFACTURING METHOD OF ABSORBENT ARTICLE

MANUFACTURING METHOD OF ABSORBENT ARTICLE

MANUFACTURING METHOD OF ABSORBENT ARTICLE

RELATED APPLICATIONS

The present application is based on, and claims priority from, Japanese Application Number 2008-271124, filed Oct. 21, 2008, the disclosure of which is hereby incorporated by reference herein in its entirety.

BACKGROUND OF THE INVENTION

1. Field of the Invention

The present invention relates to a manufacturing method of an absorbent article including a front waistband region, a rear waistband region, and a crotch region located between the front waistband region and the rear waistband region.

2. Description of the Related Art

An absorbent article, such as a disposable diaper, includes a front waistband region, a rear waistband region facing the front waistband region, and a crotch region located between the front waistband region and the rear waistband region.

A manufacturing method of such an absorbent article includes a step of bonding a continuum of the front waistband region and a continuum of the rear waistband region in predetermined regions each corresponding to a bonded region of the front waistband region and the rear waistband region after overlapping the continuum of the front waistband region and the continuum of the rear waistband region under conveyance (hereinafter, referred to as bonding step).

Conventionally, an ultrasonic bonding device has been used in the bonding step. The ultrasonic bonding device includes; an anvil roll which supports the continuum of the front waistband region and the continuum of the rear waistband region while rotating in a conveyance direction; an ultrasonic horn which applies ultrasonic vibration to each predetermined region corresponding to the bonded region of the front waistband region and the rear waistband region while pressing the predetermined region against the anvil roll; and an ultrasonic vibrator which supplies the ultrasonic vibration to the ultrasonic horn.

In order to reliably bond the continuum of the front waistband region and the continuum of the rear waistband region, the ultrasonic horn is formed to be longer than a length of the bonded region, in a direction (hereinafter, referred to as Crossing Direction (CD)) perpendicular to a conveyance direction (hereinafter, Machine Direction (MD)), of the continuum of the front waistband region and the continuum of the rear waistband region.

There is known a method of monitoring a bonded state of the continuum of the front waistband region and the continuum of the rear waistband region after such a bonding step (for example, see Japanese Patent Application Publication No. H 6-341966 (pages 2 and 3, FIGS. 1-3)). This method makes it possible to detect whether or not a failure (abnormality) has occurred in the bonded state in the bonded region by measuring a current which flows into the ultrasonic vibrator.

Meanwhile, when the ultrasonic horn presses the predetermined region against the anvil roll, the ultrasonic horn may incline with respect to the anvil roll, and thus the ultrasonic horn may become unable to press one end side in the CD of the predetermined region.

However, by the conventional method described above, even if the ultrasonic horn has inclined with respect to the anvil roll, it is determined that no failure occurs in the bonded state as long as the current satisfies a specified condition, since only the current is measured.

Therefore, the conventional method has a problem that a failure occurred in the bonded state cannot be detected in such a case. In particular, if the failure occurs in the bonded state in a disposable diaper, the disposable diaper cannot take form as a product of an underpants-type diaper; for it allows separation of a bonded region while in use, for example.

Accordingly, an object of the present invention is to provide a manufacturing method of an absorbent article capable of reliably detecting whether or not a failure has occurred in a bonded state of a predetermined region corresponding to a bonded region of a front waistband region and a rear waistband region.

SUMMARY OF THE INVENTION

In order to solve the problem described above, the present invention has the following feature. A first feature of the present invention is a manufacturing method of an absorbent article including a front waistband region (front waistband region 20A), a rear waistband region (rear waistband region 20B), and a crotch region (crotch region 30) located between the front waistband region and the rear waistband region. The method includes: a step A (bonding step) of bonding, by using an ultrasonic bonding device (for example, an ultrasonic bonding device 100), a continuum of the front waistband region and a continuum of the rear waistband region in predetermined regions each corresponding to a bonded region (bonded region 40) of the front waistband region and the rear waistband region after overlapping the continuum of the front waistband region and the continuum of the rear waistband region under conveyance; a step B (first determining step) of outputting a first predetermined signal indicating a failure state when it is determined that an output signal from the ultrasonic bonding device does not satisfy a first specified condition; and a step C (second determining step) of outputting a second predetermined signal indicating a failure state when it is determined that a bonded area in any of the predetermined regions does not satisfy a second specified condition.

According to the present invention, it is possible to provide a manufacturing method of an absorbent article capable of reliably detecting whether or not a failure has occurred in a bonded state of a predetermined region corresponding to a bonded region of a front waistband region and a rear waistband region.

DESCRIPTION OF THE PREFERRED EMBODIMENTS

First Embodiment

Figure 1:
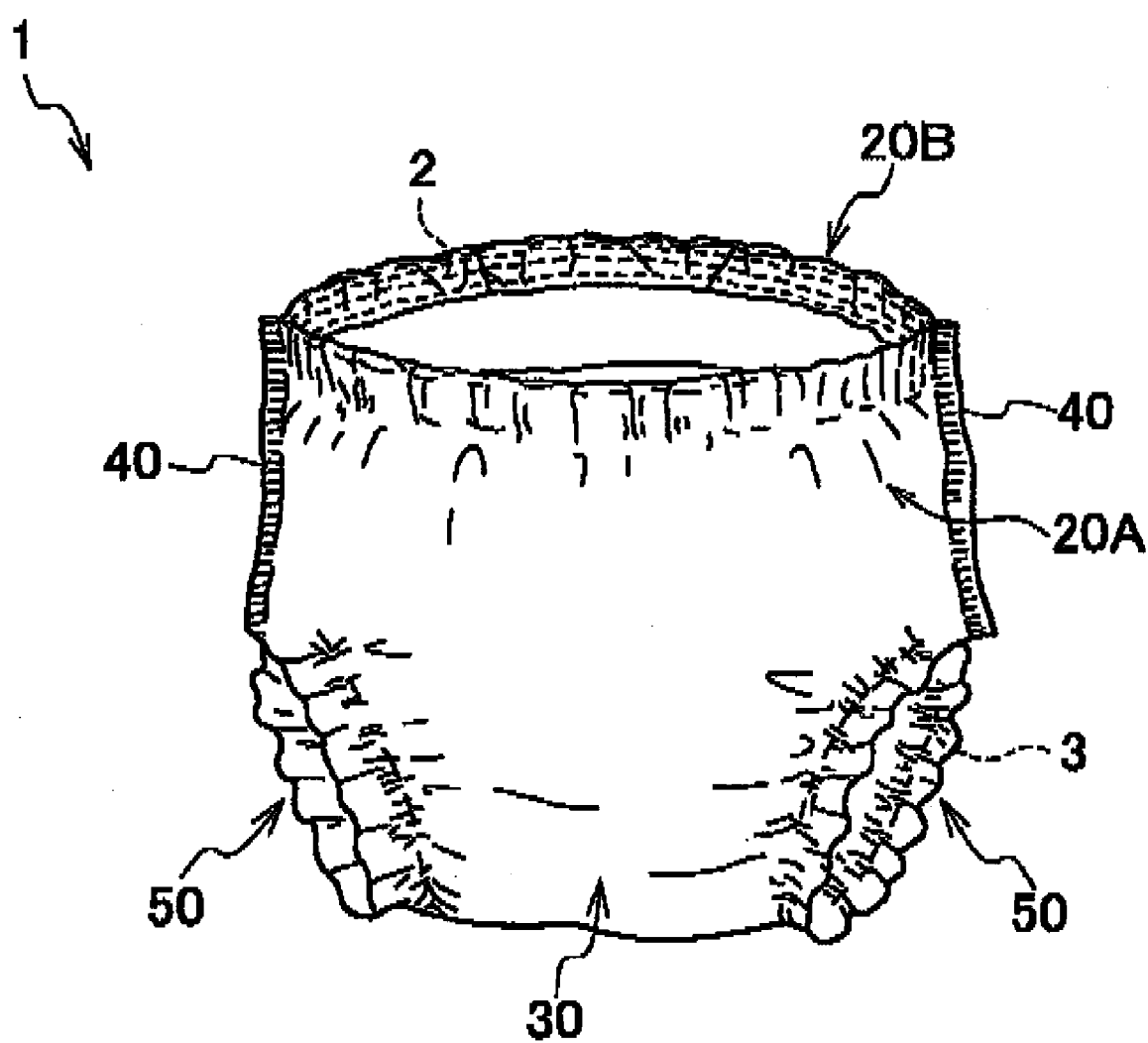
FIG. 1 is a perspective view of an absorbent article 1 according to a first embodiment.

Hereinafter, a first embodiment according to the present invention will be described with reference to the drawings. Specifically, (1) configuration of absorbent article, (2) configuration of ultrasonic bonding device, (3) working of ultrasonic bonding device, and (4) manufacturing method of absorbent article will be described.

Note that, in the description of the following drawings, the same or similar reference numerals are given to the same or similar parts. However, it should be noted that the drawings are schematic and proportions of respective dimensions and the like differ from actual ones.

Therefore, a concrete size and the like should be determined in consideration of the following description. Further, it is needless to say that the drawings contain parts where relations and proportions of the dimensions are different from one another.

(1) Configuration of Absorbent Article

First, a configuration of an absorbent article 1 according to the first embodiment will be described with reference to the drawings. FIG. 1 is a perspective view of the absorbent article 1 according to the first embodiment.

As shown in FIG. 1, the absorbent article 1 includes a front waistband region 20A, a rear waistband region 20B facing the front waistband region 20A, a crotch region 30 located between the front waistband region 20A and the rear waistband region 20B, bonded regions 40 located on right and left side portions of the front waistband region 20A and the rear waistband region 20B, and leg regions 50 located on right and left sides of the crotch region 30.

The front waistband region 20A and the rear waistband region 20B are stretchy in a conveyance direction (hereinafter, MD direction) of a continuum of the front waistband region 20A and a continuum of the rear waistband region 20B (hereinafter simply referred to as a "continuum 10"). For example, the front waistband region 20A and the rear waistband region 20B may be stretchy in the MD direction by having a fit gather 2 provided therein, and may be stretchy in the MD direction by forming the continuum 10 itself with a stretchy sheet.

The crotch region 30 is stretchy in a direction crossing perpendicularly with the MD direction (hereinafter, CD direction). For example, the crotch region 30 may be stretchy in the CD direction by having a leg gather 3 provided therein, and may be stretchy in the CD direction by forming the continuum 10 itself with a stretchy sheet.

The bonded regions 40 are regions where the front waistband region 20A and the rear waistband region 20B are bonded. The leg regions 50 are regions where the front waistband region 20A and the rear waistband region 20B open.

(2) Configuration of Ultrasonic Bonding Device

Figure 2:
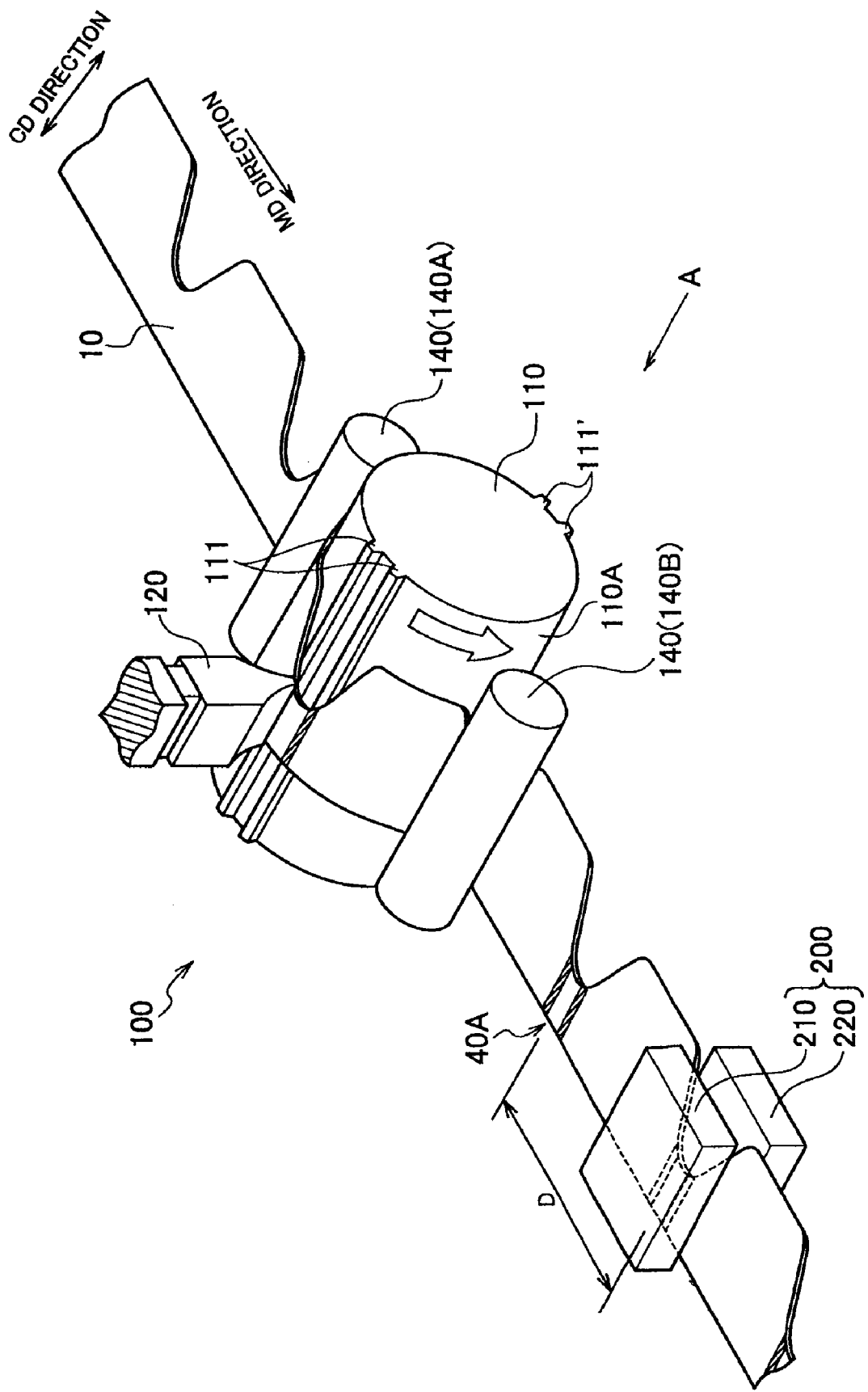
FIG. 2 is a perspective view of an ultrasonic bonding device 100 according to the first embodiment.
Figure 3:
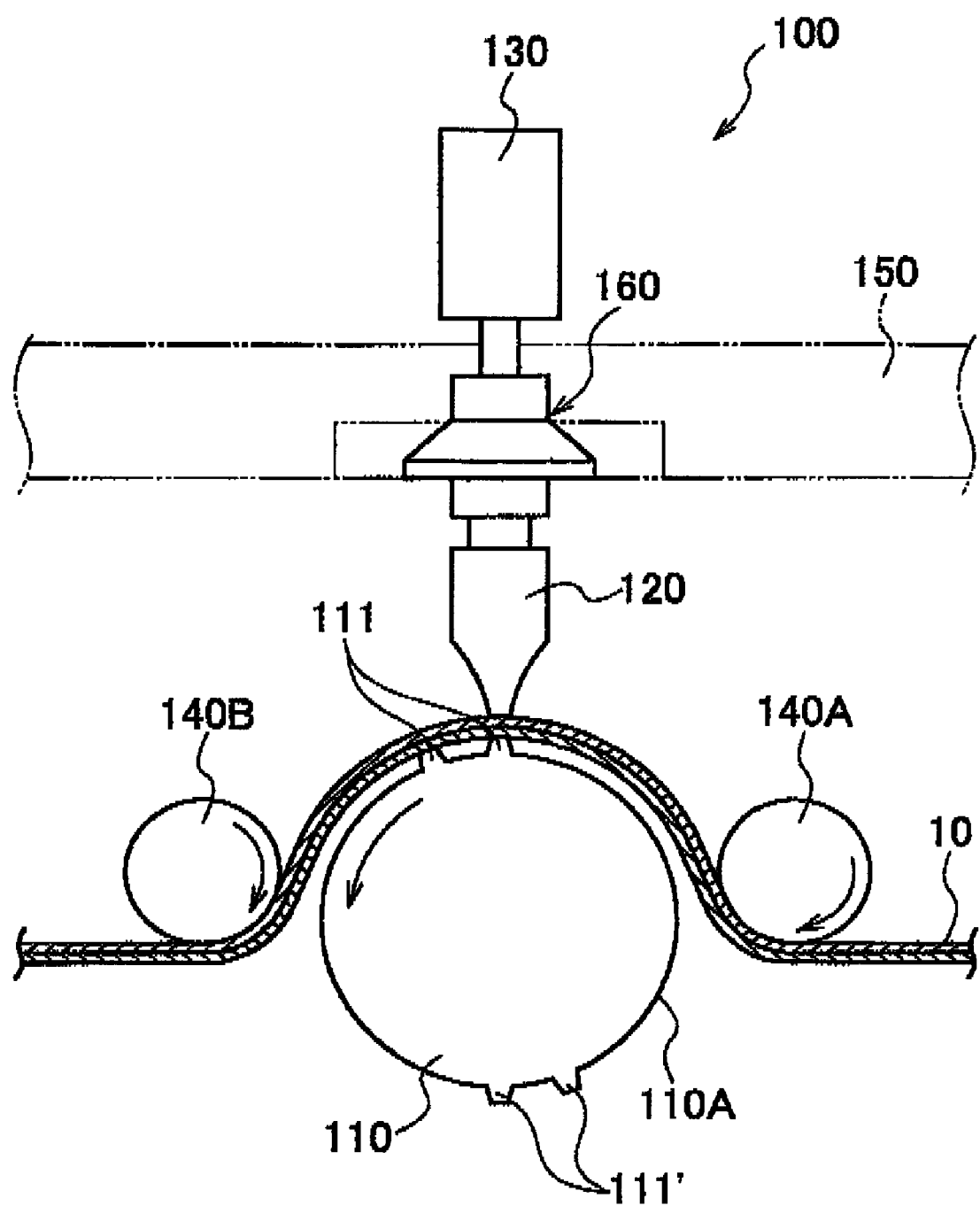
FIG. 3 is a side view (view along an arrow A of FIG. 2) of the ultrasonic bonding device 100 according to the first embodiment.
Figure 4:
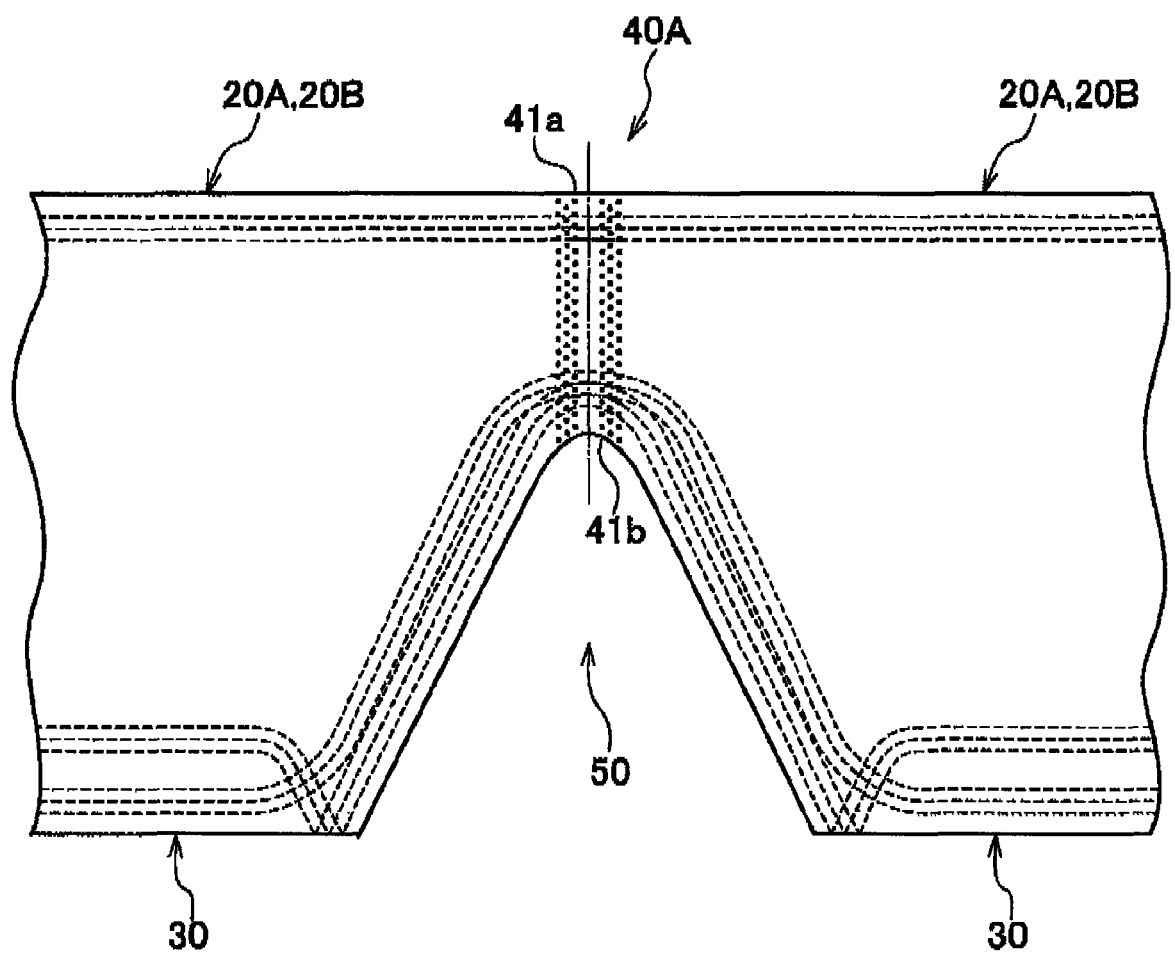
FIG. 4 is a view showing a predetermined region 40A of a continuum 10 corresponding to a bonded region 40 of the absorbent article 1 according to the first embodiment.

Next, a configuration of an ultrasonic bonding device 100 according to the first embodiment will be described with reference to the drawings. FIG. 2 is a perspective view of the ultrasonic bonding device 100 according to the first embodiment. FIG. 3 is a side view (view along an arrow A of FIG. 2) of the ultrasonic bonding device 100 according to the first embodiment. FIG. 4 is a view showing a predetermined region 40A of the continuum 10 corresponding to the bonded region 40 of the absorbent article 1 according to the first embodiment.

As shown in FIGS. 2 and 3, the ultrasonic bonding device 100 is provided with an anvil roll 110, an ultrasonic horn 120, an ultrasonic vibrator 130, and guide rolls 140.

(2-1) Anvil Roll

The anvil roll 110 rotates in the MD direction, and conveys the continuum 10 in the MD direction while supporting the continuum 10. Pairs of protruding parts 111, 111' are provided in an outer circumference 110A of the anvil roll 110, the protruding parts 111, 111' arranged to face the predetermined region 40A of the continuum 10 which corresponds to the bonded region 40 of the absorbent article 1. Here, the predetermined region 40A of the continuum 10 denotes a boundary where the continuum 10 is cut, i.e., a region where the ultrasonic horn 120 works with the protruding parts 111, 111' provided in the anvil roll 110 to pinch the continuum 10, as shown in FIG. 4.

An interval between one pair of protruding parts 111 and the other pair of protruding parts 111' corresponds to a distance D between the predetermined regions 40A of the continuum 10 (see FIG. 2). In other words, the pairs of protruding parts 111, 111' are provided in positions at one half of the diameter of the anvil roll 110, respectively. Further, the arrangement interval and the number of the pairs of protruding parts 111, 111' are chosen suitably depending on the diameter of the anvil roll 110.

(2-2) Ultrasonic Horn

The ultrasonic horn 120 presses the predetermined region 40A of the continuum 10 against the anvil roll 110, and works with the protruding parts 111, 111' to pinch the continuum 10 so that ultrasonic vibration can be applied to the predetermined region 40A of the continuum 10, the predetermined region 40A corresponding to the bonded region 40 of the absorbent article 1.

The ultrasonic horn 120 is fixed to a pressing arm 150, which adjusts a height of the ultrasonic horn 120, via a booster 160 which amplifies an ultrasonic amplitude. The ultrasonic horn 120 is connected to the ultrasonic vibrator 130 via the booster 160. The ultrasonic horn 120 comes into contact with the whole predetermined region 40A of the continuum 10.

The ultrasonic horn 120 adjusts at least one of a pressure (contact pressure) and an inclination at the time of contacting the predetermined region 40A of the continuum 10, on the basis of an output of at least one of a first predetermined signal and a second predetermined signal to be described later.

For example, when a pressure at the time of contacting the predetermined region 40A of the continuum 10 is low, the ultrasonic horn 120 adjusts the pressure to be higher. On the other hand, when a pressure at the time of contacting the predetermined region 40A of the continuum 10 is high, the ultrasonic horn 120 adjusts the pressure to be lower.

Further, when a press to one end side 41a of the predetermined region 40A in the CD direction is weak or strong, the ultrasonic horn 120 adjusts the inclination of the one end side 41a and the other end side 41b (see FIG. 4) of the predetermined region 40A in the CD direction so that the balance therebetween can be adjusted.

(2-3) Ultrasonic Vibrator

The ultrasonic vibrator 130 generates an ultrasonic vibration, and applies the ultrasonic vibration thus generated to the ultrasonic horn. The ultrasonic vibrator 130 is fixed to the pressing arm 150 via the booster 160 which amplifies the ultrasonic amplitude.

(2-4) Guide Roll

The guide roll 140 includes a first guide roll 140A which leads the continuum 10 between the anvil roll 110 and the ultrasonic horn 120, and a second guide roll 140B which leads the continuum 10 on which the ultrasonic vibration is applied at the predetermined region 40A of the continuum 10 to a next step.

Here, a monitor 200 (for example, a camera) is provided at the downstream side in the MD direction of the ultrasonic bonding device 100 (see FIG. 2), the monitor 200 monitoring the predetermined region 40A of the continuum 10 having led from the second guide roll 140B.

(2-5) Monitor

The monitor 200 includes a monitoring part 210 located above the continuum 10 under conveyance, and an illuminating part 220 located under the continuum 10 under the conveyance.

The monitoring part 210 monitors (shoots) the continuum 10 (for example, the continuum of the front waistband region 20A or the continuum of the rear waistband region 20B) under the conveyance. The illuminating part 220 illuminates the continuum 10 under the conveyance so that the monitoring part 210 may monitor the continuum 10 under the conveyance easily.

(3) Working of Ultrasonic Bonding Device

Next, a working of the ultrasonic bonding device according to the first embodiment will be described briefly. In the ultrasonic bonding device 100, the anvil roll 110 rotates in association with the conveyance of the continuum 10. The protruding parts 111, 111' also rotates with the rotation of the anvil roll 110.

The ultrasonic horn 120 works with the protruding parts 111, 111' to pinch the continuum 10 so that the ultrasonic vibration generated by the ultrasonic vibrator 130 can be applied to the predetermined region 40A of the continuum 10. Specifically, the ultrasonic vibration is converted from electrical energy by the ultrasonic vibrator 130. The ultrasonic vibration thus converted turns into a longitudinal vibration in a diameter direction of the anvil roll 110 by the ultrasonic horn 120, after the amplitude thereof is amplified via the booster 160. The ultrasonic vibration is applied to the predetermined region 40A of the continuum 10 in such a manner that a tip part on the side of the anvil roll 110 of the ultrasonic horn 120 works with the protruding parts 111 to pinch the continuum 10.

Accordingly, the ultrasonic bonding device 100 can bond the continuum of the front waistband region 20A and the continuum of the rear waistband region 20B. Note that details of the configuration or the working of the ultrasonic bonding device 100 according to the first embodiment are well-known techniques, and are described in Japanese Patent Application Publication No. 5-15551 filed by the present applicant, for example.

(4) Manufacturing Method of Absorbent Article

Figure 5:
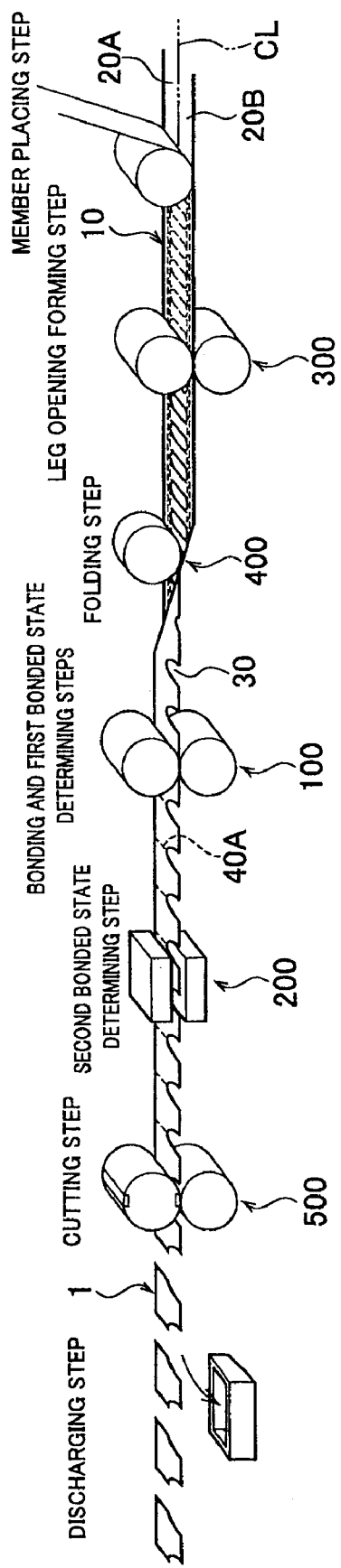
FIG. 5 is a schematic view showing a manufacturing method of the absorbent article according to the first embodiment.

Next, a configuration of a manufacturing method of an absorbent article according to the first embodiment will be described with reference to the drawings. FIG. 5 is a schematic view showing the manufacturing method of an absorbent article according to the first embodiment.

As shown in FIG. 5, the manufacturing method of an absorbent article includes at least a member placing step, a leg opening forming step, a folding step, bonding and first bonded state determining steps, a second bonded state determining step, a cutting step, and a discharging step.

(4-1) Member Placing Step

At the member placing step, various members are placed on the continuum (for example, a continuum of an outer sheet). The various members include gathers (the fit gather 2 and the leg gather 3), a tarpaulin, an absorber, and a top sheet (not shown), for example.

(4-2) Leg Opening Forming Step

At the leg opening forming step, a cut roll 300 forms the leg regions 50 (for example, leg holes) on the continuum 10 on which the various members are placed after the member placing step.

(4-3) Folding Step

At the folding step, a folding device 400 folds the continuum 10, in which the leg regions 50 are formed, into two at a center line CL of the continuum 10 in the CD direction after the leg opening forming step. In other words, the continuum of the front waistband region 20A and the continuum of the rear waistband region 20B are overlapped with each other at the folding step.

(4-4) Bonding and First Bonded State Determining Steps

At the bonding and first bonded state determining steps, the bonding step and the first bonded state determining step are simultaneously performed after the folding step.

(4-4-1) Bonding Step

At the bonding step, the ultrasonic bonding device 100 bonds the continuum of the front waistband region 20A and the continuum of the rear waistband region 20B in the predetermined region 40A of the continuum 10 corresponding to the bonded region 40 of the absorbent article 1.

At the bonding step, the ultrasonic horn 120 of the ultrasonic bonding device 100 in a state of continuously outputting an output signal to be described later comes into contact with the whole area of predetermined region 40A of the continuum 10.

(4-4-2) First Bonded State Determining Step

Figure 6:
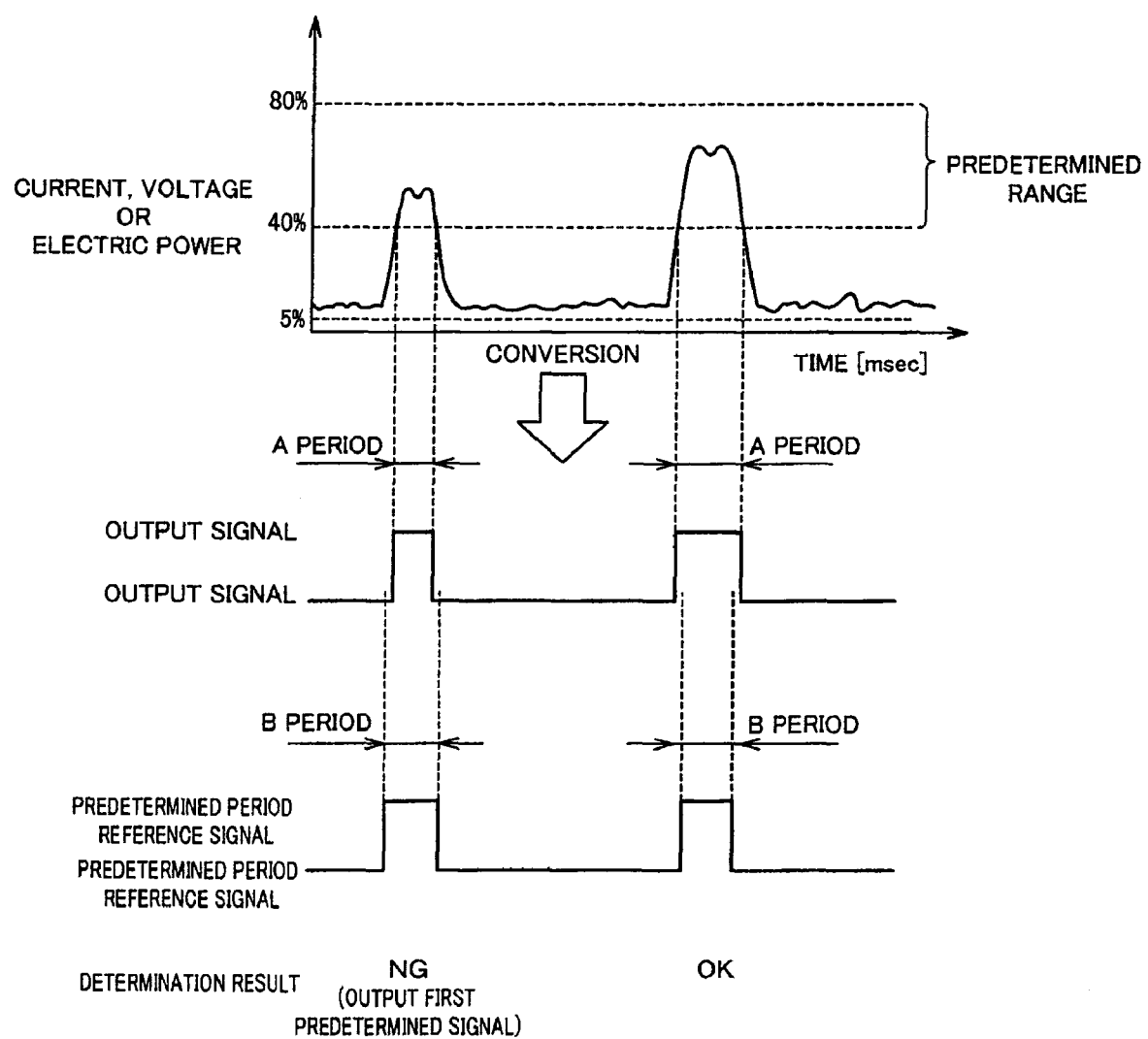
FIG. 6 is a graph showing an output signal from the ultrasonic bonding device 100 according to the first embodiment.

The first bonded state determining step will be described with reference to the drawings. FIG. 6 is a graph showing an output signal from the ultrasonic bonding device 100 according to the first embodiment.

At the first bonded state determining step, as shown in FIG. 6, the ultrasonic bonding device 100 outputs a first predetermined signal indicating a failure state when it is determined that the output signal from the ultrasonic bonding device 100 does not satisfy a first specified condition.

Here, the first specified condition indicates that the output signal from the ultrasonic bonding device 100 takes a value within a predetermined range. The predetermined range indicates a range of the output signal from the ultrasonic bonding device 100 from a middle setting to a high setting, which exceed a low setting set in advance. For example, the first specified condition indicates a value of 40 to 80% of the output signal from the ultrasonic bonding device 100.

As shown in FIG. 6, when a current, a voltage, or an electric power of the output signal takes a value out of the predetermined range (for example, 40% or less, or 80% or more) within a predetermined period, the ultrasonic bonding device 100 determines that the output signal does not satisfy the first specified condition. Further, the predetermined period indicates a period required for the ultrasonic horn 120 to apply ultrasonic vibration to the predetermined region 40A of the continuum 10 by working with the protruding parts 111, 111' provided in the anvil roll 110 to pinch the continuum 10.

For example, as shown in FIG. 6 (on the left side), when a period (A period) in which the current, the voltage, or the electric power of the output signal satisfies the predetermined range is shorter than a predetermined period (B period), the ultrasonic bonding device 100 determines that the output signal does not satisfy the first specified condition (NG), and outputs the first predetermined signal.

On the other hand, when the current, the voltage, or the electric power of the output signal takes a value within the predetermined range (for example, 40 to 80%) during the predetermined period, the ultrasonic bonding device 100 determines that the output signal satisfies the first specified condition.

For example, as shown in FIG. 6 (on the right side), when the period (A period) in which the current, the voltage, or the electric power of the output signal satisfies the predetermined range is longer than the predetermined period (B period), the ultrasonic bonding device 100 determines that the output signal satisfies the first specified condition (OK).

(4-5) Second Bonded State Determining Step

Figure 7:
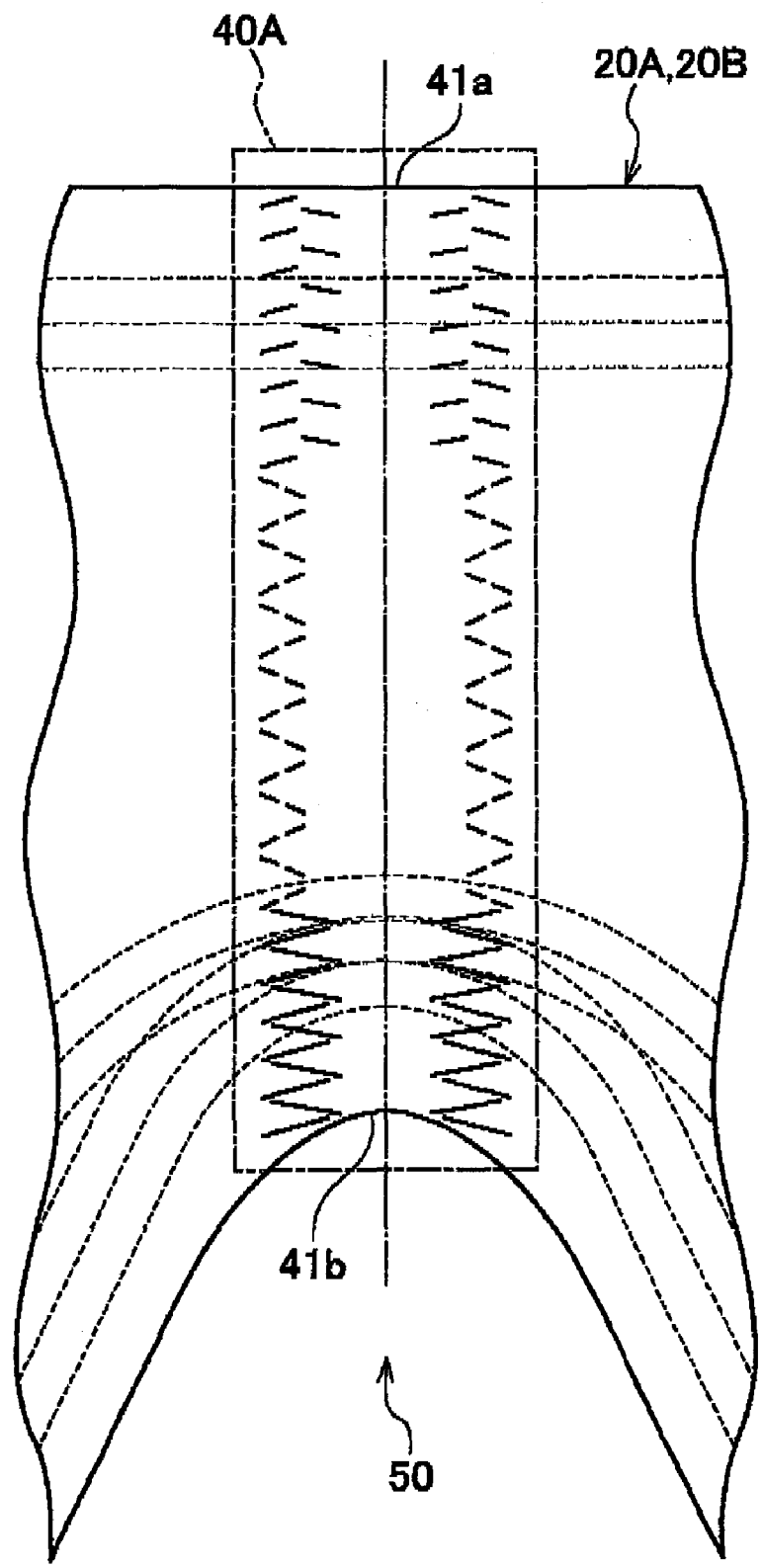
FIG. 7 is an enlarged view showing the predetermined region 40A of the continuum 10 corresponding to the bonded region 40 of the absorbent article 1 according to the first embodiment.

The second bonded state determining step will be described with reference to the drawings. FIG. 7 is an enlarged view showing the predetermined region 40A of the continuum 10 corresponding to the bonded region 40 of the absorbent article 1 according to the first embodiment.

At the second bonded state determining step, as shown in FIG. 7, the monitor 200 outputs a second predetermined signal indicating a failure state when it is determined that a bonded area in the predetermined region 40A of the continuum 10 does not satisfy a second specified condition. For example, the second specified condition indicates a bonded area in the predetermined region 40A of the continuum 10 set in advance (for example, 14% or more with respect to the predetermined region 40A (2 cm$^2$ or more of the bonded area with respect to 14.25 cm$^2$ of the predetermined region 40A)) or, a bonded range in the predetermined region 40A (for example, a range from one end side 41a to the other end side 41b in the CD direction of the predetermined region 40A).

As shown in FIG. 7, when a bonded area in a part of the predetermined region 40A of the continuum 10 is smaller than a predetermined area or out of the bonded range, the monitor 200 determines that the bonded area in the predetermined region 40A of the continuum 10 does not satisfy the second specified condition. On the other hand, when the bonded area in the part of the predetermined region in the predetermined 40A of the continuum 10 is not smaller than the predetermined area or within the bonded range, the monitor 200 determines that the bonded area in the predetermined region 40A of the continuum 10 satisfies the second specified condition.

Here, the ultrasonic horn 120 of the ultrasonic bonding device 100 can adjust at least one of the pressure and the inclination at the time of coming into contact with the predetermined region 40A of the continuum 10, on the basis of the output of at least one of the first predetermined signal and the second predetermined signal, as described above.

(4-6) Cutting Step

At the cutting step, after the bonded state determining steps, a cutting device 500 cuts in the CD direction the predetermined region 40A of the continuum 10 corresponding to the bonded region 40 of the absorbent article 1 in order to form the absorbent article 1 (see FIG. 1).

(4-7) Discharging Step

At the discharging step, after the cutting step, the absorbent article 1, which corresponds to at least one of the first predetermined signal outputted from the ultrasonic bonding device 100 and the second predetermined signal outputted from the monitor 200, among the absorbent articles 1 is discharged. In other words, when neither the first predetermined signal nor the second predetermined signal is outputted, the absorbent article 1 which is an end product is formed.

Here, the continuum 10 conveyed after the bonding step is conveyed in a state where the continuum of the front waistband region 20A and the continuum of the rear waistband region 20B are bonded. For example, the continuum of the front waistband region 20A and the continuum of the rear waistband region 20B are conveyed in the state of being bonded, between the bonding step and the bonded state determining steps, between the bonded state determining steps and the cutting step, and between the cutting step and the discharging step.

In the first embodiment, the first bonded state determining step and the second bonded state determining step are performed. Thereby, it is possible to determine whether or not the output signal from the ultrasonic bonding device 100 satisfies the first specified condition, and whether or not the bonded area in the predetermined region 40A of the continuum 10 satisfies the second specified condition. Thus, it is possible to monitor the output signal from the ultrasonic bonding device 100 and the bonded area in the predetermined region 40A of the continuum 10. Accordingly, compared with a case where only the output signal from the ultrasonic bonding device 100 is monitored and a case where only the bonded area in the predetermined region 40A is monitored, whether or not a failure has occurred in the bonded state of the predetermined region 40A of the continuum 10 can be reliably detected.

Here, in the conventional technique, when the ultrasonic horn 120 inclines with respect to the anvil roll 110, it is determined that no failure occurs in the bonded state as long as the current satisfies the specified condition, since only the current is measured.

For this reason, there has been a problem that the conventional technique fails to detect the inclination of the ultrasonic horn 120 with respect to the anvil roll 110 and thus to detect the occurrence of a failure in the bonded state. Accordingly, one end side in the CD direction of the predetermined region 40A is not bonded, thereby causing the manufacturing failure of the absorbent article 1.

On the other hand, in the first embodiment, even in a case where the ultrasonic horn 120 inclines with respect to the anvil roll 110, whether or not a failure has occurred in the bonded state of the predetermined region 40A of the continuum 10 can be instantly detected, without failing to detect the inclination of the ultrasonic horn 120 with respect to the anvil roll 110.

Further, even if the condition of the pressure between the ultrasonic horn 120 and the protruding parts 111, 111' is not satisfied in a state where the ultrasonic horn 120 does not incline with respect to the anvil roll 110, whether or not a failure has occurred in the bonded state of the predetermined region 40A of the continuum 10 can be instantly detected, without failing to detect that the pressure condition is not satisfied.

Thus, it is possible to prevent the manufacturing failure of the absorbent article 1 due to an event where one end side in the CD direction of the predetermined region of the continuum 10 is not bonded.

In the first embodiment, by performing the discharging step after the cutting step, it is possible to discharge the absorbent article 1 in which a failure has occurred in the bonded state of the predetermined region, and thereby to reliably prevent the manufacturing failure of the absorbent article 1.

In the first embodiment, the ultrasonic horn 120 adjusts at least one of the pressure and the inclination at the time of contacting the predetermined region 40A of the continuum 10 on the basis of the output of at least one of the first predetermined signal and the second predetermined signal. Thereby, the manufacturing failure of the absorbent article 1 can be reduced.

Second Embodiment

Hereinafter, a second embodiment according to the present invention will be described with reference to the drawings. Specifically, (1) configuration of ultrasonic bonding device, (2) working of ultrasonic bonding device, (3) manufacturing method of absorbent article, and (4) operation and effect will be described. Note that, the same reference numerals are given to the same parts as the ultrasonic bonding device according to the first embodiment described above, and different parts will be mainly described.

(1) Configuration of Ultrasonic Bonding Device

Figure 8:
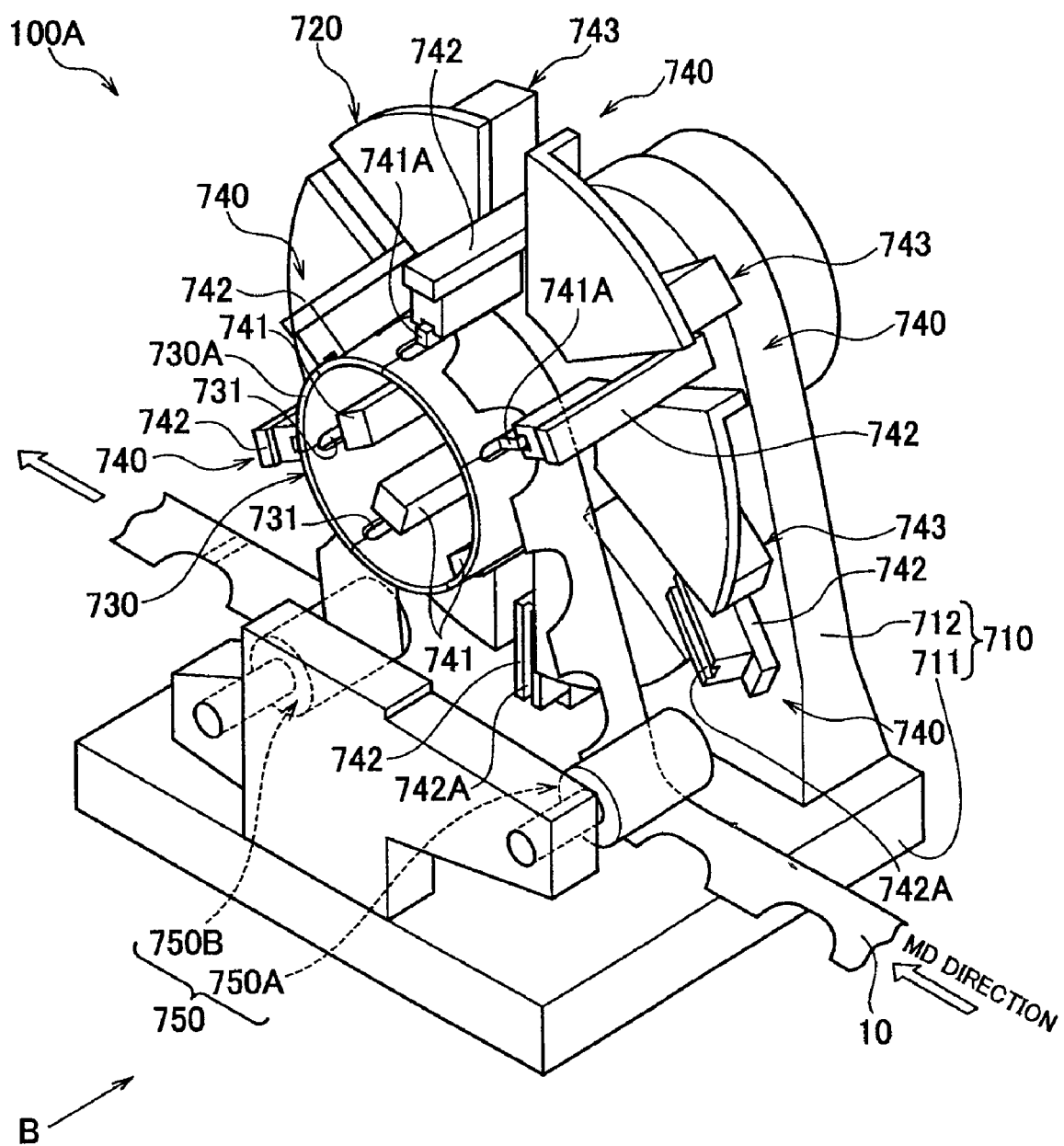
FIG. 8 is a perspective view showing an ultrasonic bonding device 100A according to a second embodiment.
Figure 9:
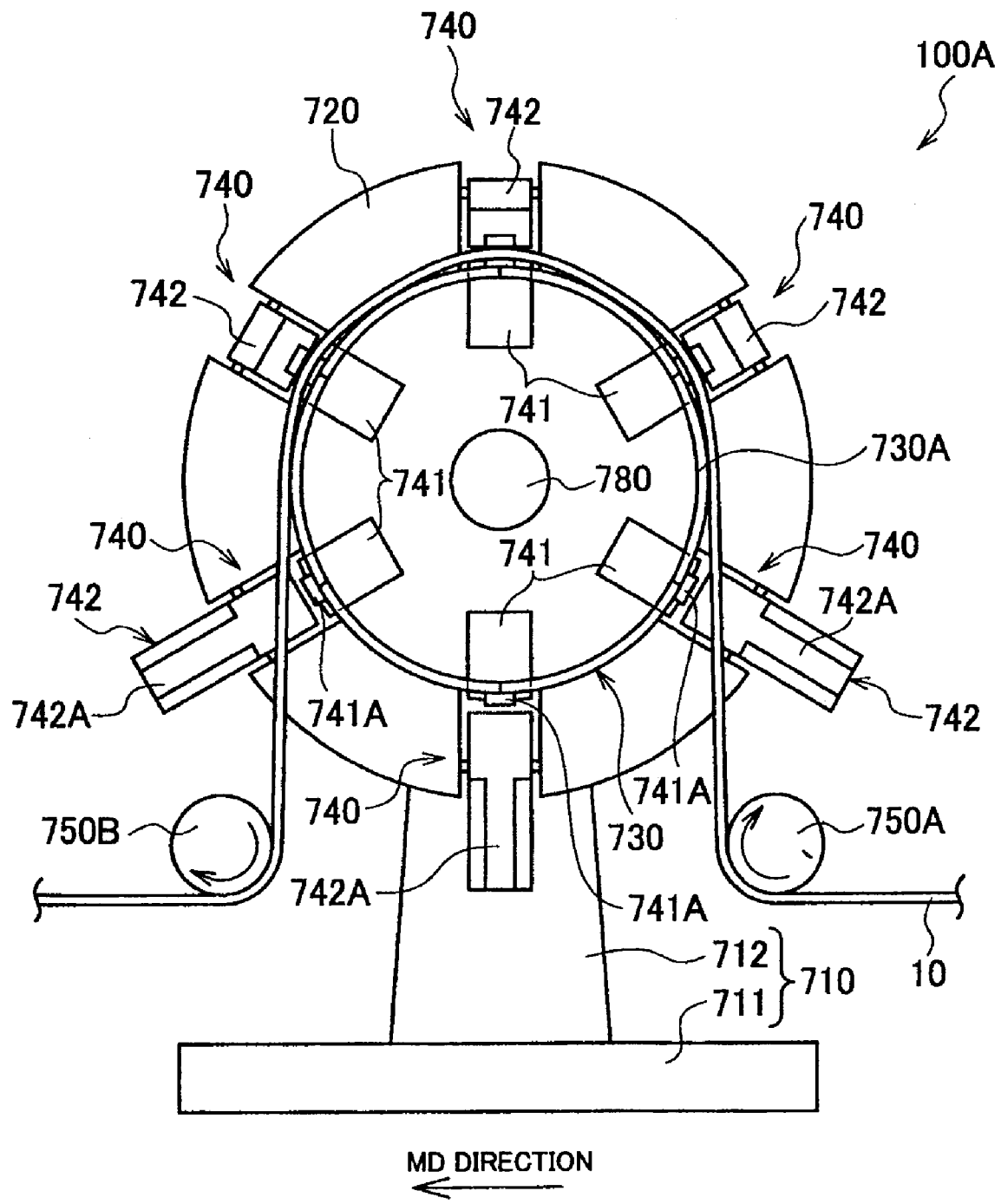
FIG. 9 is a side view (view along an arrow B of FIG. 8) showing the ultrasonic bonding device 100A according to the second embodiment.

First, a configuration of an ultrasonic bonding device 100A according to the second embodiment will be described with reference to the drawings. FIG. 8 is a perspective view showing the ultrasonic bonding device 100A according to the second embodiment. FIG. 9 is a side view (view along an arrow B of FIG. 8) showing the ultrasonic bonding device 100A according to the second embodiment.

As shown in FIGS. 8 and 9, the ultrasonic bonding device 100A includes a supporting base 710, a rotating disk 720, a drum 730, clamping units 740, and a guide roll 750.

(1-1) Supporting Base

The supporting base 710 includes a supporting base 711 fixed on the foundation of a production line, and a supporting frame 712 provided vertically in a standing manner from the supporting base 711.

(1-2) Rotating Disk

The rotating disk 720 is provided on the front side panel (at the near side in FIG. 8) of the supporting frame 712. The rotating disk 720 rotates via a bearing (not shown) or the like centering on a rotation center shaft 780 (see FIG. 9) which is rotatable with respect to the supporting frame 712.

(1-3) Drum

The drum 730 is provided concentrically with the rotating disk 720. The drum 730 is a cylindrical body rotating together with the rotating disk 720. A continuum 10 is wound around a part of an outer circumference surface (at the upper part in the drawing) of the drum 730.

The drum 730 is formed of six equal arcuate split pieces 730A into which the drum 730 is divided in the circumference direction of the drum 730. Each of the arcuate split pieces 730A is attached to the rotating disk 720 via a stay (not shown). A through hole 731 through which an ultrasonic horn 741A of a fixed arm 741 to be described later can pass is formed in each of the arcuate split pieces 730A.

The drum 730 can respond to various product sizes of the absorbent article 1 by changing a drum with a small diameter, a middle diameter, a large diameter or the like in accordance with a size of the absorbent article 1 (for example, various product sizes, such as "S", "M", and "L").

(1-4) Clamping Unit

The clamping unit 740 is formed of six clamping units 740 provided radially on the back side panel of the rotating disk 720 (at the far side in FIG. 8). The clamping unit 740 includes a fixed arm 741, and a swinging arm 742.

The clamping unit 740 is slidably provided in the diameter direction of the drum 730. In other words, as described above, when the fixed arm 741 and the attaching position of the fixed arm 741 are changed depending on the outer diameter size of the drum 730 mounted on the rotating disk 720, the attaching position of the clamping unit 740 is also changed.

(1-4-1) Fixed Arm

The fixed arms 741 are provided on the inner circumference side of the drum 730. The fixed arm 741 rotates together with the rotating disk 720 and the drum 730. The ultrasonic horn 741A which oscillates an ultrasonic wave is formed in each of the fixed arms 741.

The ultrasonic horn 741A comes into contact with the continuum 10 by passing through the through hole 731 formed in the drum 730, and projecting from the outer circumference surface of the drum 730. Here, the ultrasonic horn 741A comes into contact with the whole predetermined region 40A of the continuum 10 corresponding to the bonded region 40 of the absorbent article 1.

(1-4-2) Swinging Arm

The swinging arms 742 are swingably provided at positions facing the fixed arms 741 with the drum 730 interposed therebetween. The swinging arm 742 swings (opens and closes) depending on the rotating position of the drum 730 by a cam mechanism 743. The swinging arm 742 rotates together with the rotating disk 720 and the drum 730 in a similar manner as the fixed arm 741. An anvil 742A which pinches the whole predetermined region 40A of the continuum 10 in cooperation with the ultrasonic horn 741A is provided in the swinging arm 742.

The swinging arm 742 swings to the side of the drum 730 (the continuum 10) so that the anvil 742A may come into contact with the continuum 10. Here, the anvil 742A comes into contact with the whole predetermined region 40A of the continuum 10. Accordingly, the continuum 10 is clamped by the fixed arm 741 and the swinging arm 742.

(1-5) Guide Roll

The guide roll 750 includes a pair of first guide roll 750A and a second guide roll 750B, the first guide roll 750A leading the continuum 10 on the drum 730, the second guide roll 750B leading the continuum 10 in which the ultrasonic vibration is applied to the predetermined region 40A of the continuum 10 to a next step.

Here, a monitor 200 (not shown in FIGS. 8 and 9, see FIGS. 2 and 4) which monitors the predetermined region 40A of the continuum 10 corresponding to the bonded region 40 of the absorbent article 1 having led from the second guide roll 750B is provided at the downstream side in the MD direction of the ultrasonic bonding device 100A, in the similar manner as the first embodiment.

(2) Working of Ultrasonic Bonding Device

Next, a working of the ultrasonic bonding device 100A according to the second embodiment will be described briefly. In the ultrasonic bonding device 100A, the rotating disk 720, the drum 730, and the clamping unit 740 (the fixed arm 741 and the swinging arm 742) rotate in association with the conveyance of the continuum 10.

The ultrasonic horn 741A and the anvil 742A come into contact with (faces) each other with pinching the predetermined region 40A of the continuum 10 therebetween when the swinging arm 742 becomes in a closed state in accordance with the rotating position of the drum 730. The ultrasonic horn 741A and the anvil 742A apply the ultrasonic vibration to the predetermined region of the continuum 10 corresponding to the bonded region 40 of the absorbent article 1.

Accordingly, the ultrasonic bonding device 100A can bond the continuum of the front waistband region 20A and the continuum of the rear waistband region 20B. Note that details of the configuration, the working, or the like of the ultrasonic bonding device 100A according to the second embodiment are well-known techniques, and are described in Japanese Patent Application No. 2005-212149 filed by the present applicant, for example.

(3) Manufacturing Method of Absorbent Article

Next, a configuration of the manufacturing method of the absorbent article according to the second embodiment will be described. The manufacturing method of the absorbent article includes at least a member placing step, a leg opening forming step, a folding step, bonding and first bonded state determining steps, a second bonded state determining step, a cutting step, and a discharging step in the similar manner as the first embodiment.

Note that since other steps except the bonding and first bonded state determining steps in the second embodiment are the same as those of the first embodiment, description thereof will be omitted.

(3-1) Bonding Step

At the bonding step, after the folding step, the ultrasonic bonding device 100A bonds the continuum of the front waistband region 20A and the continuum of the rear waistband region 20B in the predetermined region 40A of the continuum 10 corresponding to the bonded region 40 of the absorbent article 1.

At the bonding step, the ultrasonic horn 741A and the anvil 742A come into contact with the whole predetermined region 40A of the continuum 10. Further, at the bonding step, the ultrasonic horn 741A and the anvil 742A output an output signal to be described later, while contacting the whole predetermined region 40A of the continuum 10.

(3-2) First Bonded State Determining Step

Figure 10:
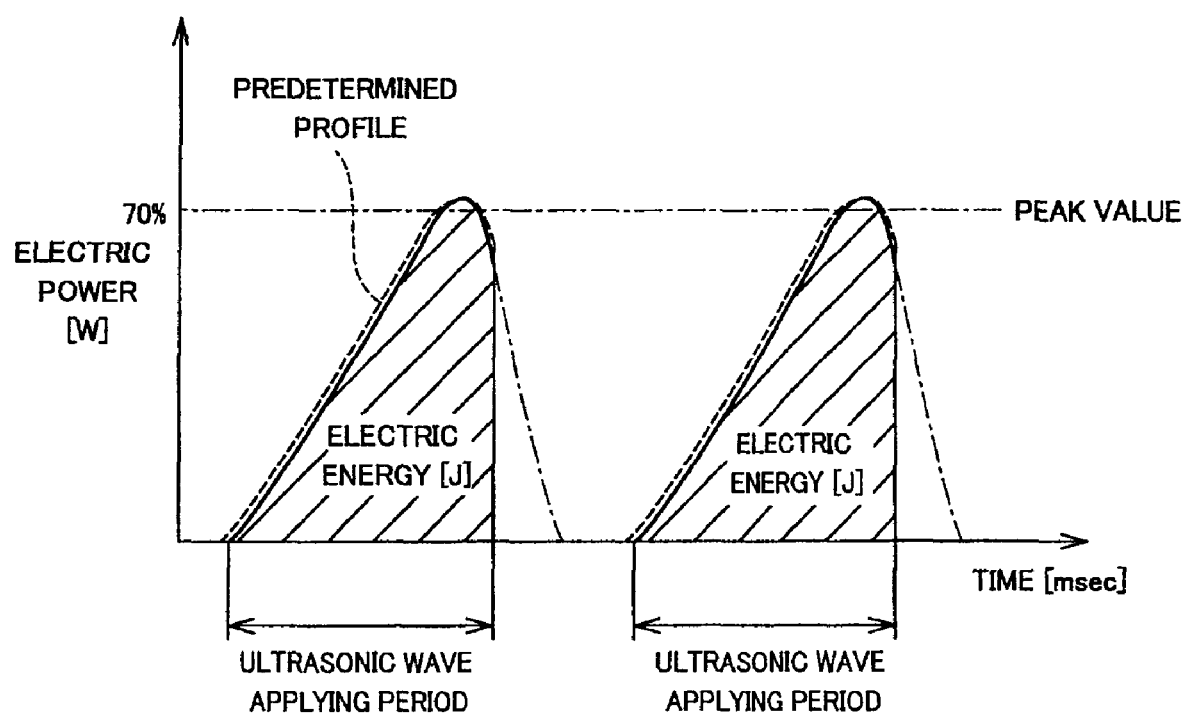
FIG. 10 is a graph showing an output signal from the ultrasonic bonding device 100A according to the second embodiment.

Next, the first bonded state determining step will be described with reference to the drawings. FIG. 10 is a graph showing an output signal from the ultrasonic bonding device 100A according to the second embodiment.

As shown in FIG. 10, the ultrasonic bonding device 100A outputs a first predetermined signal indicating a failure state when it is determined that the output signal from the ultrasonic bonding device 100A does not satisfy a first specified condition.

As shown in FIG. 10, when a peak value of the electric power of the output signal does not reach a predetermined value (electric power set in advance (for example, 70% or more)) within a predetermined period, the ultrasonic bonding device 100A determines that the output signal does not satisfy the first specified condition. On the other hand, when the peak value of the electric power of the output signal reaches the predetermined value within the predetermined period, the ultrasonic bonding device 100A determines that the output signal satisfies the first specified condition.

Further, as shown in FIG. 10, when electric energy of the output signal does not reach a predetermined value (electric energy J set in advance (for example, 70J)) within a predetermined period, the ultrasonic bonding device 100A determines that the output signal does not satisfy the first specified condition. On the other hand, when the electric energy of the output signal reaches the predetermined value within the predetermined period, the ultrasonic bonding device 100A determines that the output signal satisfies the first specified condition.

Furthermore, as shown in FIG. 10, when a profile of the electric power of the output signal does not correspond with a predetermined profile (a profile set in advance) within a predetermined period, the ultrasonic bonding device 100A determines that the output signal does not satisfy the first specified condition. On the other hand, when the profile of the electric power of the output signal mostly corresponds with the predetermined profile within the predetermined period, the ultrasonic bonding device 100A determines that the output signal satisfies the first specified condition.

Here, in FIG. 10, as a period of applying ultrasonic vibration to the predetermined region of the continuum 10 (ultrasonic applying period), the application of the ultrasonic vibration is terminated when the electric energy of the output signal reaches the predetermined value. However, it is not limited to this.

For example, the application of the ultrasonic vibration may be terminated when the peak value of the electric power of the output signal reaches the predetermined value, or the application of the ultrasonic vibration may be terminated when the profile of the electric power of the output signal mostly corresponds with the predetermined profile for the time period set in advance.

When the first specified condition is not satisfied at the first bonded state determining step within the predetermined period during which the bonding step described above is carried out (i.e., when a failure of the bonded state is detected), the ultrasonic horn 741A stops applying the ultrasonic vibration to the predetermined region 40A of the continuum 10 after the predetermined period, releases the contact with the predetermined region 40A, and outputs the first predetermined signal.

On the other hand, when the first specified condition is satisfied at the first bonded state determining step within the predetermined period during which the bonding step described above is carried out (i.e., when the failure of the bonded state is not detected), the ultrasonic horn 741A stops applying the ultrasonic vibration to the predetermined region 40A of the continuum 10, or releases the contact with the predetermined region 40A.

According to the second embodiment, the same operation and effect as the first embodiment can be acquired. Particularly, since the peak value of the electric power of an output signal, the electric energy of the output signal, and the profile of the electric power of the output signal can be monitored, whether or not the failure has occurred in the bonded state of the predetermined region 40A of the continuum 10 can be detected further reliably.

Other Embodiment

As described above, the contents of the present invention has been disclosed through the embodiments of the present invention. However, it should not be understood that the statement and the drawings which make a part of this disclosure limit the present invention. Various alternative embodiments, examples, and operational techniques will be apparent to those skilled in the art from this disclosure.

For example, the embodiments of the present invention can be changed as follows. Specifically, an ultrasonic bonding device is not limited to the ultrasonic bonding device 100 described in the first embodiment, or the ultrasonic bonding device 100A described in the second embodiment. It is needless to say that a device may be used which can apply ultrasonic vibration to the predetermined region 40A of the continuum 10 corresponding to the bonded region 40 of the absorbent article 1.

Thus, the present invention naturally includes various embodiments and the like which have not been described here. Therefore, the technical scope of the present invention is defined only by the invention specific matter according to the appended claims which are appropriate from the above-described description.

What is claimed is:

1. A manufacturing method of an absorbent article including a front waistband region, a rear waistband region, and a crotch region located between the front waistband region and the rear waistband region, the method comprising:
    a step A of bonding, by using an ultrasonic bonding device, a continuum of the front waistband region and a continuum of the rear waistband region in predetermined regions each corresponding to a bonded region of the front waistband region and the rear waistband region after overlapping the continuum of the front waistband region and the continuum of the rear waistband region under conveyance;
    a step B of outputting a first predetermined signal indicating a failure state when it is determined that an output signal from the ultrasonic bonding device does not satisfy a first specified condition; and
    a step C of outputting a second predetermined signal indicating a failure state when it is determined that a bonded area in any of the predetermined regions does not satisfy a second specified condition.

2. The manufacturing method of an absorbent article according to claim 1, further comprising the steps of:
    conveying the continuum of the front waistband region and the continuum of the rear waistband region in a bonded state;
    cutting the predetermined regions of the continuum of the front waistband region and the continuum of the rear waistband region in a direction crossing a conveyance direction of the continuum of the front waistband region and the continuum of the rear waistband region in order to form the absorbent articles; and
    discharging an absorbent article corresponding to at least one of the outputted first predetermined signal and second predetermined signal.

3. The manufacturing method of an absorbent article according to claim 1, wherein
    in the step A, an ultrasonic horn of the ultrasonic bonding device continuously outputting the output signal is brought into contact with the whole area of each predetermined region, and
    in the step B, it is determined that the output signal does not satisfy the first specified condition when any of a current, a voltage, and an electric power of the output signal takes a value out of a predetermined range within a predetermined period.

4. The manufacturing method of an absorbent article according to claim 1, wherein
    in the step A, an ultrasonic horn of the ultrasonic bonding device is brought into contact with the whole area of each predetermined region;
    in the step A, the ultrasonic horn of the ultrasonic bonding device outputs the output signal while being brought into contact with the whole area of each predetermined region; and
    in the step B, it is determined that the output signal does not satisfy the first specified condition in any of cases where any of a peak value and electric energy of electric power of the output signal does not reach a predetermined value within a predetermined period, and where a profile of the electric power of the output signal does not correspond with a predetermined profile within the predetermined period.

5. The manufacturing method of an absorbent article according to claim 1, wherein
    in the step C, it is determined that the bonded area in the predetermined region satisfies the second specified condition when a bonded area in a part of the predetermined region is not smaller than a predetermined area.

6. The manufacturing method of an absorbent article according to claim 1, wherein
    an ultrasonic horn of the ultrasonic bonding device adjusts at least one of a pressure and an inclination at the time of coming into contact with each predetermined region on the basis of the output of at least one of the first predetermined signal and the second predetermined signal.

7. The manufacturing method of an absorbent article according to claim 4, wherein
    when the first specified condition is not satisfied in the step B within a predetermined period during which the step A is carried out, the ultrasonic horn stops applying ultrasonic vibration to the predetermined region after the predetermined period, releases the contact with the predetermined region, and outputs the first predetermined signal; and
    when the first specified condition is satisfied in the step B within the predetermined period during which the step A is carries out, the ultrasonic horn stops applying the ultrasonic vibration to the predetermined region or releases the contact with the predetermined region.

* * * * *